US005455643A

United States Patent [19]

Ki-Ho

[11] Patent Number: 5,455,643

[45] Date of Patent: Oct. 3, 1995

[54] INSTRUMENT FOR IMPROVING EYESIGHT AND COLOR VISION

[76] Inventor: Seong Ki-Ho, 25-1, Shinsul-dong, Dongdemoon-gu, Seoul, Rep. of Korea

[21] Appl. No.: 187,460

[22] Filed: Jan. 28, 1994

[30] Foreign Application Priority Data

Jan. 28, 1993 [KR] Rep. of Korea ........................ 93-1023

[51] Int. Cl.[6] ........................................................ A61B 3/00

[52] U.S. Cl. ............................................ 351/203; 351/221

[58] Field of Search .................................... 351/200, 203, 351/221, 214

[56] References Cited

U.S. PATENT DOCUMENTS 4,940,323 7/1990 Downing ................................ 351/203

*Primary Examiner*—William L. Sikes

*Assistant Examiner*—Huy Mai

*Attorney, Agent, or Firm*—Dennison, Meserole, Pollack & Scheiner

[57] ABSTRACT

The present invention relates to an instrument for improving eyesight and color-blindness, more specifically, to an instrument for improving or recovering weakened eyesight or color-blindness of a person. The instrument includes a sphere-shaped member having a plurality of apertures. There is an apparatus for emanating visible ray into the eyeball. Support means attaches to the member as does an eyepiece consisting of a light-transmitting plate and a plurality of LEDs. There is a case for protecting the light-transmitting plate and a plurality of light-transmitting holes which are equipped with plates in red, green and colorless or clear. The instrument also includes a sensor for preventing sleepiness and a driving section. There is a motor driving the light-transmitting plate. The instrument also includes lighting and fire-extinguishing equipment with a carbon point and a sound amplifier.

2 Claims, 4 Drawing Sheets

INSTRUMENT FOR IMPROVING EYESIGHT AND COLOR VISION

FIELD OF THE INVENTION

The present invention relates to an instrument for improving eyesight and color vision. More specifically, the invention relates to an instrument for improving or recovering the eyesight and color vision of a person.

BACKGROUND OF THE INVENTION

Therapeutics for weakened-eyesight are numerous. The primary method is to strengthen ciliary muscles of the eyeball. This helps control functions of the crystalline lens such as in eyeball gymnastics. Another method is to use a concave lens and/or a convex lens.

Causes of amblyopia are various, but one cannot depend on the known methods of treatment for improving weak eyesight. In particular, symptoms of amblyopia by cataract were thought to be incurable. As for treatment of these symptoms, the obsolete way of therapeutics is not acceptable.

Emmetropia is when the eye is in focus, and ametropia is when the total refractive index of an eye is out of harmony with the axis of the eyeball. There are three kinds of ametropia, i.e. myopia, hypermetropia and astigmatism.

Causes of mytropia are various. Generally, some people read a book for a long time and their distance vision is effected. Thus, that person is liable to develop mytropia. Mytropia is an immovable state where the crystalline lens is in a state of tension with a ciliary muscle. Mytropia is classed in various ways, i.e. malignant myopia and pseudomyopia, etc.

On the other hand, hypermetropia is a symptom were the image of a body is located at the back of the retina. Repeatedly, metropia, as well as hypermetropia, is basically caused by the abnormal symptom of the crystalline lens. Also, it is known that cataracts cause amblyopia.

SUMMARY OF THE INVENTION

It is accordingly an object of the present invention to provide an instrument for improving weakened-eyesight by strengthening of a ciliary muscle using muscular movement and irradiation of a visible ray to the eyeball.

Another object of the invention is to provide an instrument for improving color vision without difficulty by the interchanging of colored and transparent plates.

A further object of the invention is to provide an instrument for improving eyesight of persons with poor eyesight as well as persons who are color blind.

Still another object of this invention is to provide an instrument for improving eyesight and color vision, which includes a sound amplifier for preventing sleepiness from a tedious treatment and informing a treatment order.

Other objects and advantages of the invention will be made apparent as the description progresses.

DESCRIPTION OF THE INVENTION

Figure 1:
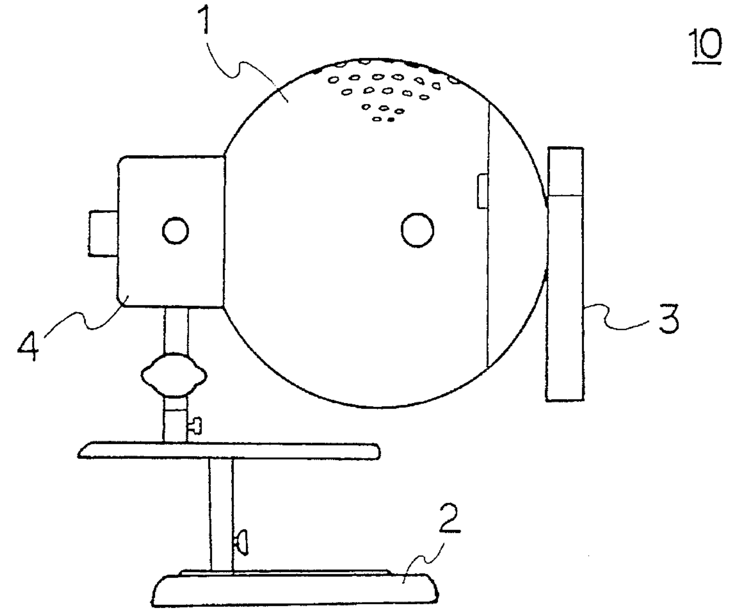
FIG. 1 is a side view showing an instrument for improving eyesight and color vision according to the present invention.
Figure 2A:
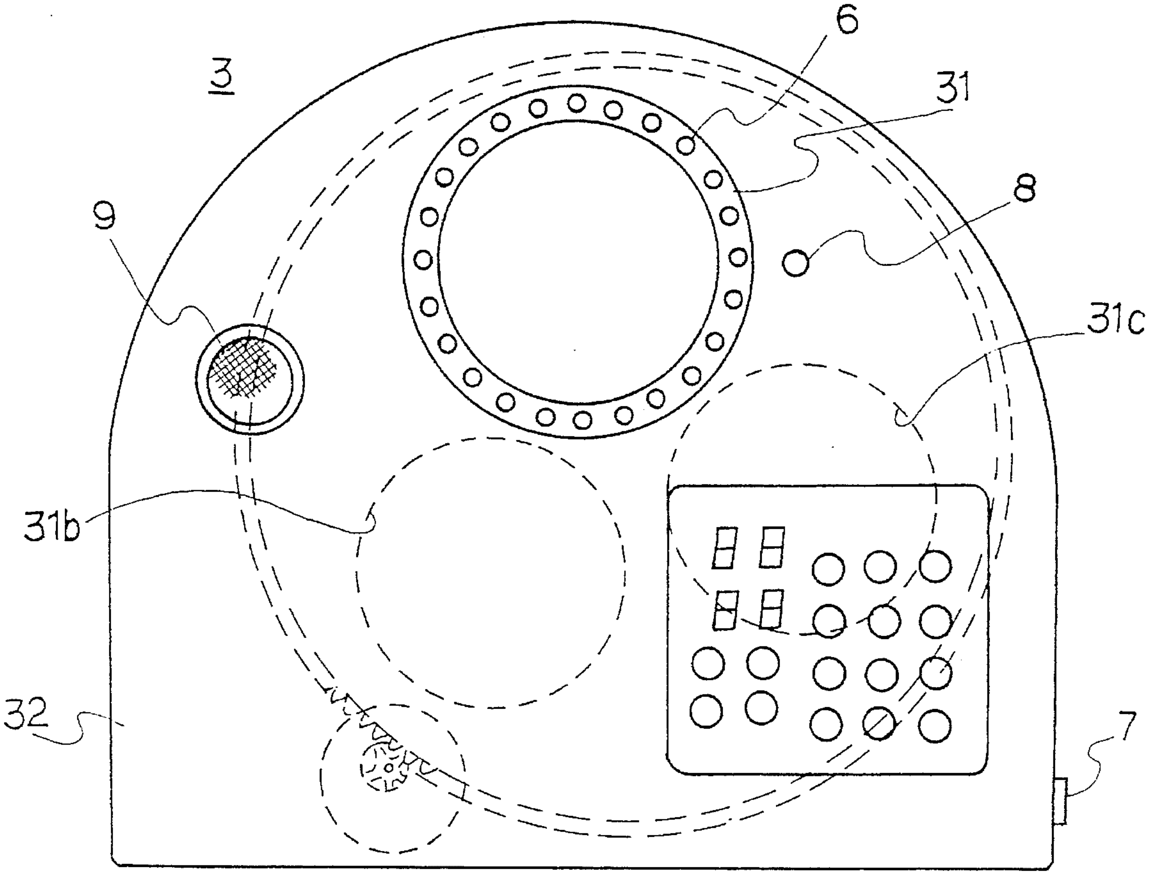
FIG. 2A is a front view showing an eyepiece of FIG. 1.
Figure 2B:
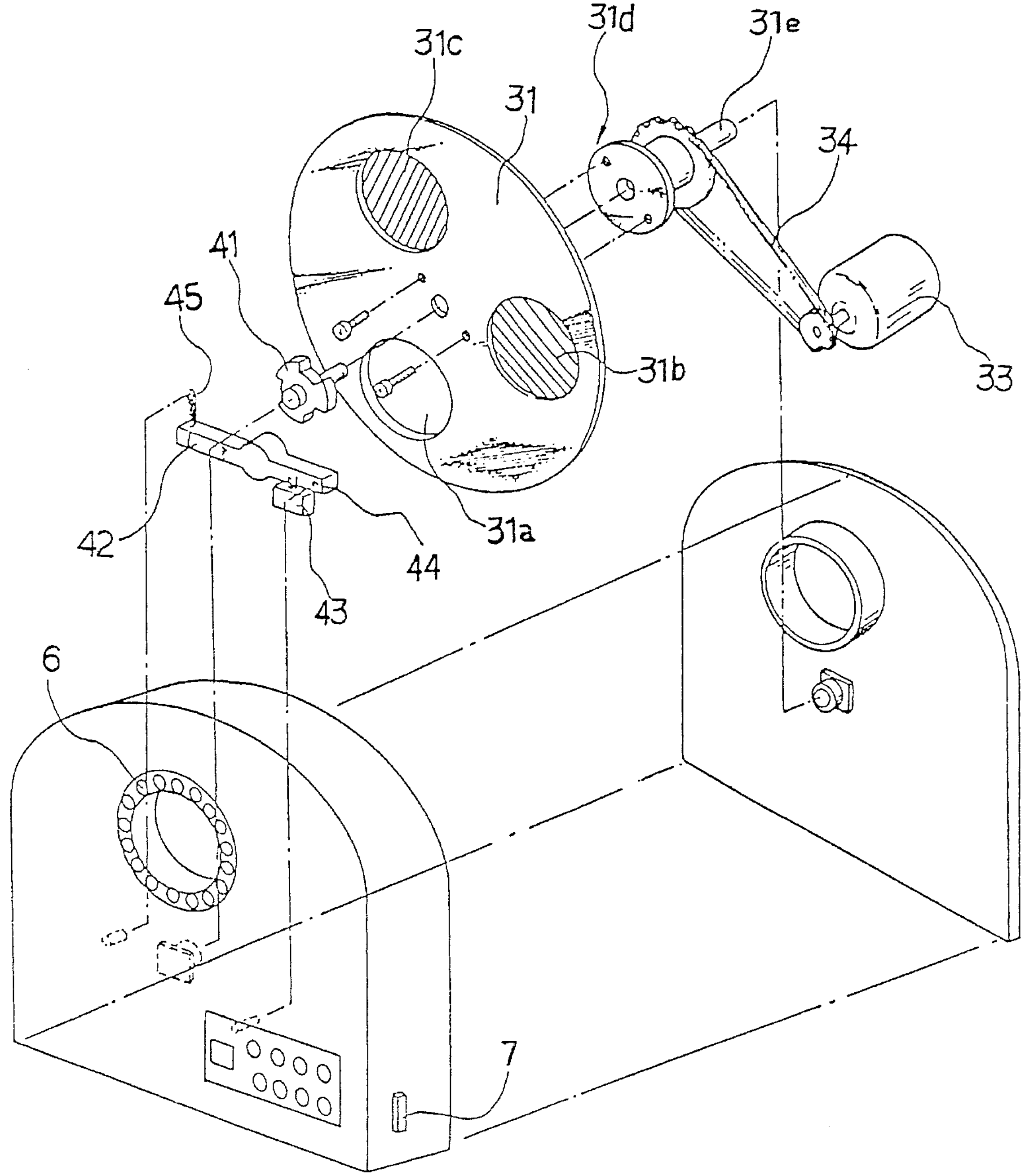
FIG. 2B is an exploded view of the eyepiece of FIG. 1.

FIG. 1 illustrates an instrument 10 for improving eyesight and color vision, according to the present invention. The instrument comprises a sphere-shaped member 1 having a plurality of apertures. The sphere-shaped member 1 is rotably attached to an apparatus 4. The apparatus 4 provides a visible ray. Also, attached to the member 1 is an eyepiece 3. The eyepiece 3 consists of a light-transmitting plate 31, a case 32 having an incident hole in the center, which protects the light-transmitting plate 31, and a motor 33 for driving the light-transmitting plate 31. The light-transmitting plate 31 is driven by the motor 33 and emanates a light which can be either a green color, a red color or clear depending on the filter. The light comes from a source of light. The transmitted light reaches the patient through an aligned incident hole or aperture in the sphere 1. With reference to FIGS. 2A and 2B, an automatic control means controls the rotary motion of the light-transmitting plate 31 which is driven by motor 33. The eyepiece 3 consists of three light-transmitting holes 31*a*, 31*b* and 31*c*. They are positioned around the circumference of light-transmitting plate 31 which is in the shape of a circle. The holes 31*a*, 31*b* and 31*c* are in trisection and have filters in red color, green color and/or colorless or clear.

The eyepiece 3 consists of the light-transmitting plate 31, the case 32 for protecting the light-transmitting plate 31 and the motor 33 which drives the light-transmitting plate 31. The light-transmitting plate 31 consists of three circular light-transmitting filters 31*a*, 31*b*, 31*c* and the circular driving section 31*d*. It is installed, in the preferred embodiment, so as to rotate around a centering pivot 31*e* within the case 32. Chain 34 connects the light-transmitting plate 31 and a driving wheel of the motor 33. The plate 31 is rotated by the motor 33. Therefore, the light-transmitting plate 31 revolves on pivot 31*e*.

Figure 3:
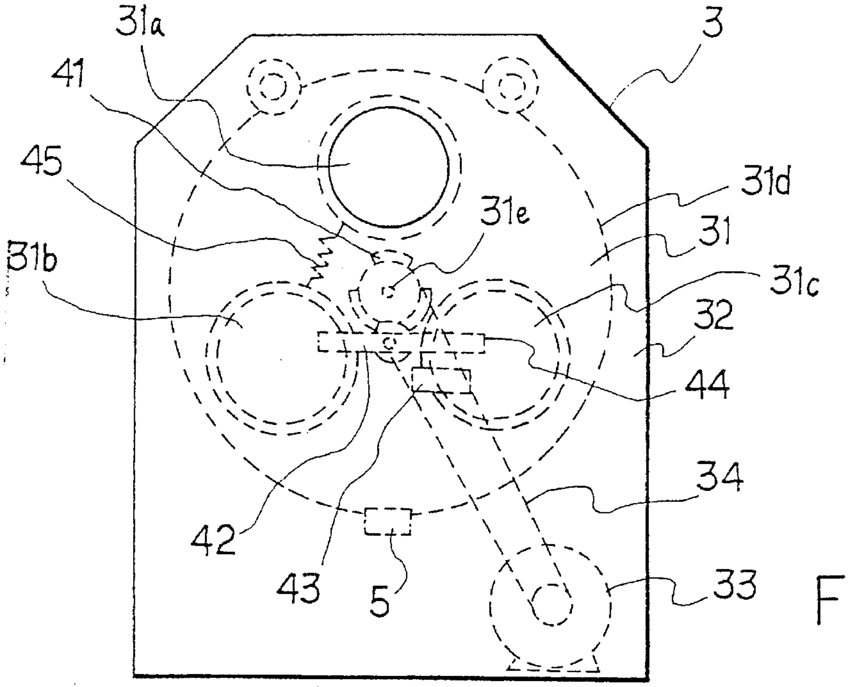
FIG. 3 is a rear view showing the eyepiece of FIG. 2.
Figure 4A:
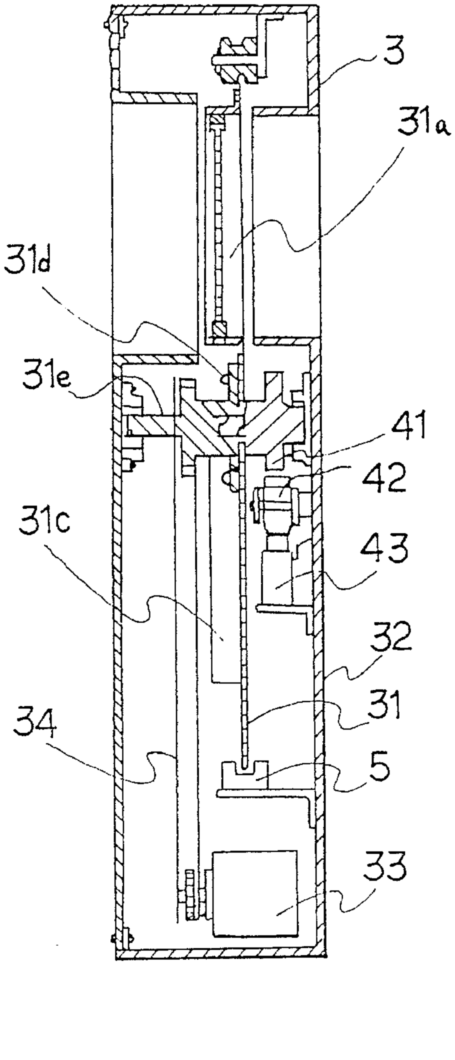
FIG. 4A is a sectional view on the line I—I of FIG. 3.
Figure 4B:
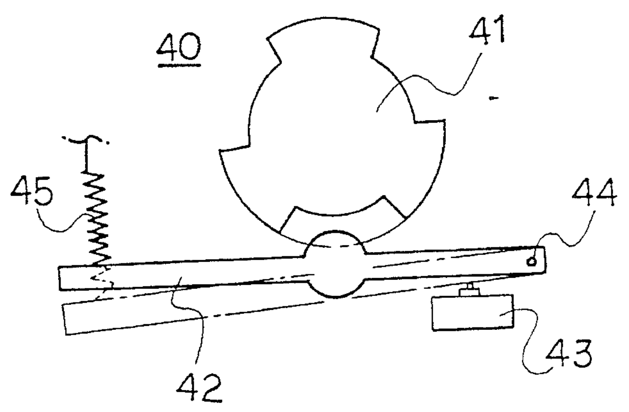
FIG. 4B is a view of the mechanical features as set forth in the present invention.

With reference to FIGS. 3, 4A and 4B, the light-transmitting plate 31 is controlled by the controller 40. The controller 40 generally includes a cam 41 mounted to the centering pivot 31*e* of light-transmitting plate 31, a driving part 42 operating by the cam 41, and a limit switch 43. One end of the driving part 42 is rotably fixed to a pivot 44 and another end is movably held by a spring 45. The driving part 42 is turned on or off by the limit switch 43. When the driving part 42 is turned on, there is action with pivot 44 and rotary motion through motor 33.

In other words, cam 41 revolves with light transmitting plate 31. Limit switch 43 turns off, when cam 41 is located at a top dead center position. At this position, motor 33 turns off. Next, limit switch 43 turns on, and cam 41 revolves down to a bottom dead center position. During this movement, the driving section 31*d* and the three light-transmitting holes 31*a*, 31*b*, 31*c*, which were located at the upper front part of the case 32 of light-transmitting plate 31, rotate. Additionally, the disk position sensor 5 which is fully equipped is around the lower part of the light-transmitting plate 31.

Figure 5:
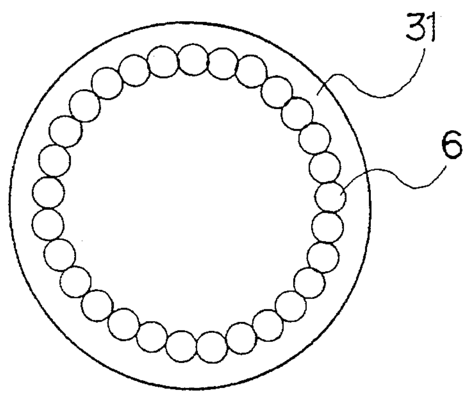
FIG. 5 is a front view showing a driving section of the invention.

The light-transmitting plate 31 is an opaque disk with three light-transmitting holes 31*a*, 31*b*, 31*c* having colored filters for transmitting a light therethrough. FIG. 5 shows a number of light emitting diodes (LEDs) 6 arranged around the circumference of a circle on the light-transmitting plate 31. It lights up when LEDs 6 have aligned with the incident hole in a straight line and lights are out when passed by the limit switch 43.

Figure 6:
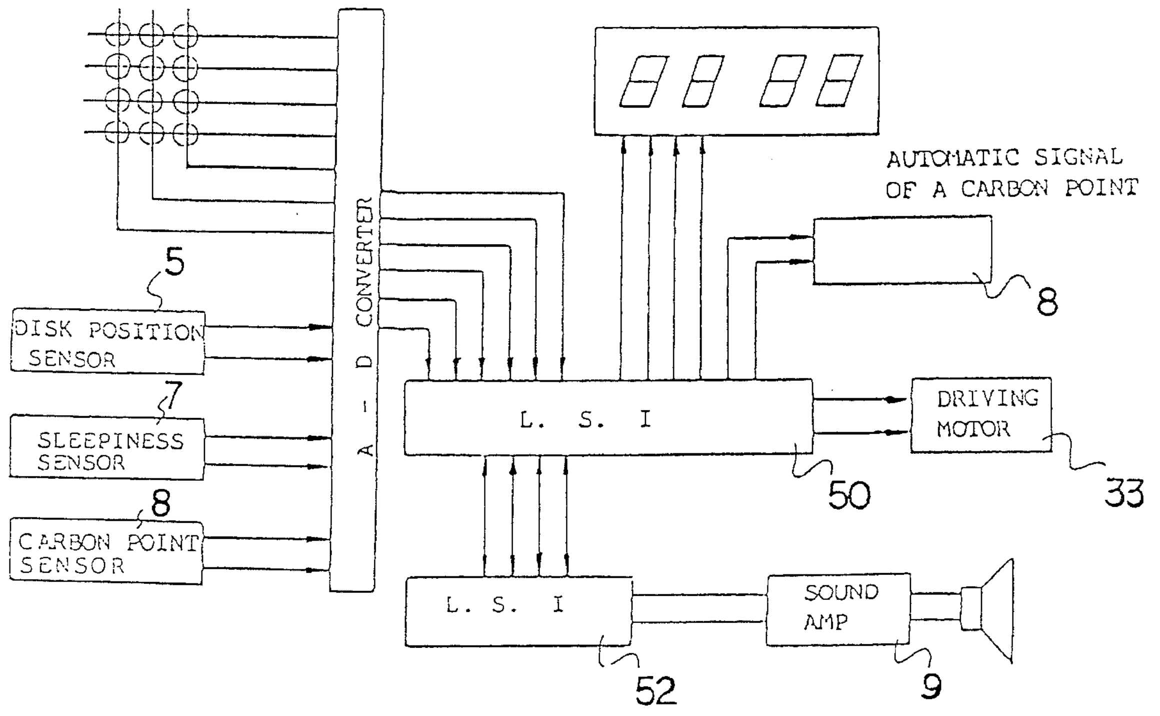
FIG. 6 is an electric circuit diagram showing the electronic apparatus of the instrument for improving eyesight and curing color vision according to the invention.

FIG. 6 illustrates the electronic circuit of the instrument which includes a sound amplifier 9, a sensor 7 for preventing sleepiness, and a sensor 8 for perceiving the combustion of a carbon point. These are positioned on case 32. Both L.S.I.s 50 and 52 shown in FIG. 6 are off-the-shelf controllers. The Central Processor 50 has a part number 87C51 and is commonly known as MICOM I.C. The other controller 52 has a part number of 16C54.

The carbon point 8 maintains the position through the sensing of the flow of an electric current. At the time of pressing the program selection switch 43, the carbon point sensor 8 and the light transmitter operate. The sound device 9 provides instructions and the sleepiness sensor 7 gives a warning sound.

The overall operation is as follows:

By the revolution of motor 33, the light-transmitting plate 31 and cam 41 rotate at once. On the revolution of the light-transmitting plate 31, one of driving section 31*d* and light-transmitting holes 31*a*, 31*b*, 31*c*, coincided with an incident hole of case 32, and motor 33 is turned off through cam 41 by limit switch 43. In this case, the patient moves his eyeball in the lighting order of LEDs 6 circularly positioned around the light-transmitting plate 31 of driving section 31*d*. In other words, the patient moves his eyeball on all sides, and the ciliary muscle of the eyeball moves quickly during this action. At the same time, a visible ray is irradiated to patient's eyeball through the incident hole, and then, the ciliary muscle is promoted into action. The patient practices the above action repeatedly and his eyesight improves through emmetropia.

In the treatment of a patient with color-blindness, the color vision is cured by irradiating the eyeball with a light in the colors of red, green and even a colorless light. This is accomplished when one of the light-transmitting holes 31*a*, 31*b*, 31*c* is located in a straight line to the source of a light or the incident hole.

Sensor 7 is for preventing sleepiness, during treatment. The sensor 7 perceives a patient's sleepiness and drives an alarm through a sound amplifier 9. A lighting and fire-extinguishing equipment 8 has a carbon point for controlling the illumination of the light. Therefore, the patient has to receive the improving effects to contrive the combustion according to his symptoms. In other words, the patient would be receiving treatment, using the alarm to prevent sleepiness, and a signal determining treatment is sounded from the sound amplifier 9 during a specified period of time.

The present invention provides an instrument for improving eyesight and color vision. It is a great convenience for improving color-blindness, because a light is exchanged selectively in color or colorless.

Although one embodiment of the present invention has been disclosed and described, it is apparent that other embodiments and modification of the invention are possible.

What is claimed is:

1. An instrument for improving eyesight and color vision by exercising a ciliary muscle of an eye, said instrument comprising:

- a sphere-shaped member having a plurality of apertures, and having an electronic apparatus for emanating a visible ray;
- support means connected to said electronic apparatus for providing support to said instrument;
- an eyepiece consisting of a light-transmitting plate having plurality of light-transmitting holes, each said hole receiving a light selected from the group consisting of red, green and clear, and said plate having a plurality of LEDs;
- a case for protecting said light-transmitting plate;
- a sensor for preventing sleepiness;
- a driving section connected to a motor for driving said light-transmitting plate; and
- a sound amplifier connected to said sleep sensor for providing an alarm.

2. An instrument according to claim 1, wherein said light irradiating through said three light transmitting holes for improving eyesight and color vision by exercising the ciliary muscle of the eye.

* * * * *